(12) United States Patent
Calvosa et al.

(10) Patent No.: US 9,827,016 B2
(45) Date of Patent: Nov. 28, 2017

(54) MODULAR VERTEBRAL STABILIZER

(71) Applicant: Lanx S.R.L., Medolla (IT)

(72) Inventors: Giuseppe Calvosa, Pisa (IT); Patrizio Cervellini, Vicenza (IT); Miria Tenucci, Lucca (IT)

(73) Assignee: Lanx S.R.L. (IT)

( * ) Notice: Subject to any disclaimer, the term of this patent is extended or adjusted under 35 U.S.C. 154(b) by 0 days.

(21) Appl. No.: 14/828,714

(22) Filed: Aug. 18, 2015

(65) Prior Publication Data

US 2015/0351803 A1 Dec. 10, 2015

Related U.S. Application Data

(63) Continuation of application No. 13/132,732, filed as application No. PCT/EP2009/067203 on Dec. 15, 2009, now abandoned.

(51) Int. Cl.
*A61B 17/70* (2006.01)

(52) U.S. Cl.
CPC ...... *A61B 17/7002* (2013.01); *A61B 17/7007* (2013.01); *A61B 17/7031* (2013.01)

(58) Field of Classification Search
CPC ............ A61B 17/7007; A61B 17/7008; A61B 17/704; A61B 17/705; Y10T 403/589; Y10T 403/4608
See application file for complete search history.

(56) References Cited

U.S. PATENT DOCUMENTS 5,207,678 A    5/1993  Harms et al.
5,275,600 A    1/1994  Allard et al.
5,312,405 A    5/1994  Korotko et al.
6,171,311 B1 * 1/2001  Richelsoph ........ A61B 17/7049
                                                606/250
6,328,740 B1   12/2001 Richelsoph
(Continued)

FOREIGN PATENT DOCUMENTS

WO    WO-0018312 A1    4/2000
WO    WO-0183212 A1    11/2001
(Continued)

OTHER PUBLICATIONS

"U.S. Appl. No. 13/132,732, Advisory Action dated Aug. 20, 2013", 3 pgs.
(Continued)

*Primary Examiner* — Jan Christopher Merene
*Assistant Examiner* — Atiya Mahmud
(74) *Attorney, Agent, or Firm* — Schwegman Lundberg & Woessner, P.A.

(57) ABSTRACT

A stabilizer device for the spinal column, comprising a first body (2) and a second body (2) adapted to be mutually connected by a rod-like element (5), the first and second bodies (2) being adapted to be fitted around first and second pedicle screws (3), which are adapted to be inserted in turn in two mutually adjacent vertebrae, the first and second bodies (2) being fixable on the pedicle screws (3), the first and second bodies (2) being fork-shaped and adapted to accommodate locking means (20), the locking means (20) being adapted to pass from a position for accommodating the pedicle screw (3) to a position for locking the pedicle screw (3) within the fork-shaped body (2).

11 Claims, 2 Drawing Sheets

(56) References Cited

U.S. PATENT DOCUMENTS

| | | | |
|---|---|---|---|
| 6,355,038 B1 | 3/2002 | Pisharodi | |
| 6,669,697 B1* | 12/2003 | Pisharodi | A61B 17/7007 606/250 |
| 6,902,565 B2 | 6/2005 | Berger et al. | |
| 6,966,910 B2 | 11/2005 | Ritland | |
| 8,114,133 B2 | 2/2012 | Logan | |
| 2003/0153912 A1* | 8/2003 | Graf | A61B 17/7007 606/256 |
| 2003/0191469 A1 | 10/2003 | Ralph et al. | |
| 2008/0172093 A1* | 7/2008 | Nilsson | A61B 17/7049 606/250 |
| 2008/0177315 A1* | 7/2008 | Usher | A61B 17/7052 606/253 |
| 2008/0215095 A1 | 9/2008 | Biedermann et al. | |
| 2008/0255619 A1 | 10/2008 | Schneiderman et al. | |
| 2009/0088800 A1 | 4/2009 | Blain et al. | |
| 2009/0326588 A1 | 12/2009 | Felix et al. | |
| 2012/0078309 A1 | 3/2012 | Calvosa et al. | |

FOREIGN PATENT DOCUMENTS

| | | |
|---|---|---|
| WO | WO-2007060534 A2 | 5/2007 |
| WO | WO-2008124196 A2 | 10/2008 |
| WO | WO-2010069964 A1 | 6/2010 |

OTHER PUBLICATIONS

"U.S. Appl. No. 13/132,732, Examiner Interview Summary dated Dec. 3, 2014", 3 pgs.

"U.S. Appl. No. 13/132,732, Final Office Action dated Mar. 13, 2015", 11 pgs.

"U.S. Appl. No. 13/132,732, Final Office Action dated Apr. 4, 2013", 14 pgs.

"U.S. Appl. No. 13/132,732, Non Final Office Action dated Jul. 18, 2012", 13 pgs.

"U.S. Appl. No. 13/132,732, Non Final Office Action dated Oct. 2, 2014", 12 pgs.

"U.S. Appl. No. 13/132,732, Preliminary Amendment filed Jun. 3, 2011", 2 pgs.

"U.S. Appl. No. 13/132,732, Response filed Aug. 2, 2013 to Final Office Action dated Apr. 4, 2013", 10 pgs.

"U.S. Appl. No. 13/132,732, Response filed Sep. 4, 2013 to Advisory Action dated Aug. 20, 2013", 9 pgs.

"U.S. Appl. No. 13/132,732, Response filed Nov. 24, 2014 to Non Final Office Action dated Oct. 2, 2014", 11 pgs.

"U.S. Appl. No. 13/132,732, Response filed Dec. 18, 2012 to Non Final Office Action dated Jul. 18, 2012", 10 pgs.

"European Application Serial No. 09801433.5, Decision to Grant dated Oct. 24, 2013", 2 pgs.

"European Application Serial No. 09801433.5, Office Action dated Jul. 28, 2011", 2 pgs.

"European Application Serial No. 09801433.5, Response filed Jan. 25, 2012 to Office Action dated Jul. 28, 2011", 9 pgs.

"International Application Serial No. PCT/EP2009/067203, International Preliminary Report on Patentability dated Jun. 30, 2011", 7 pgs.

"International Application Serial No. PCT/EP2009/067203, International Search Report dated Feb. 23, 2010", 3 pgs.

"International Application Serial No. PCT/EP2009/067203, Written Opinion dated Feb. 23, 2010", 5 pgs.

* cited by examiner

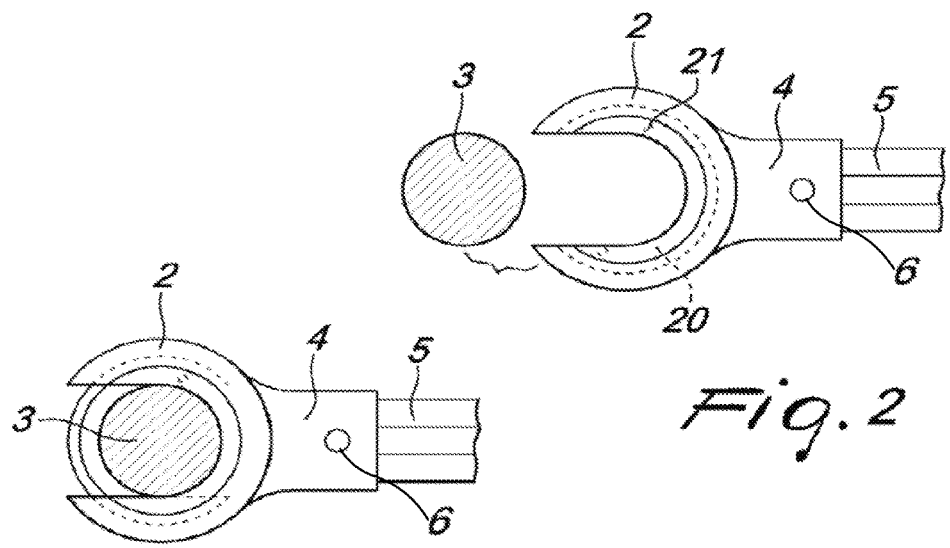
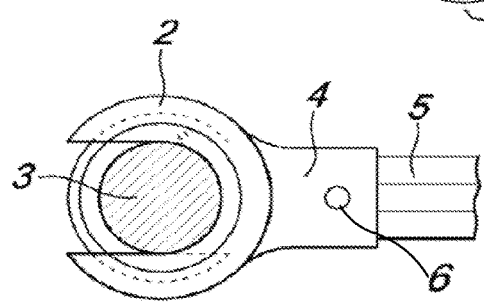
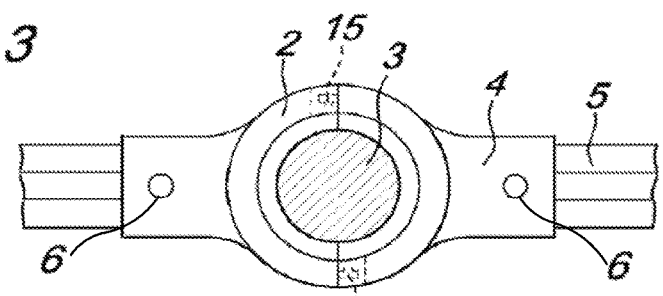
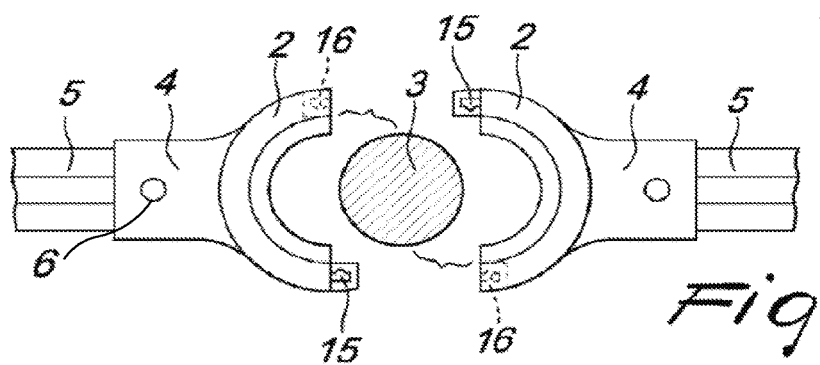

MODULAR VERTEBRAL STABILIZER

TECHNICAL FIELD

The present invention relates to a modular vertebral stabilizer. More particularly, the invention relates to a modular vertebral stabilizer that is adapted to mutually connect at least two adjacent vertebrae by using at least two connecting elements which can prevent or allow some certain limited movement to the vertebrae.

BACKGROUND ART

As is known, many pathologies related to the functionality of the spinal column are treated by total or partial immobilization, particularly with a technique known as intervertebral arthrodesis, with the aid of connection means and/or with the addition of portions of bone tissue which join such adjacent vertebrae.

Vertebral stabilization devices of the static and dynamic types are known in the art and have a screw that is adapted to be connected to a vertebra and rigid elements or elements that have a limited mobility, which have two ends which are jointly connected to the two screws connected to two adjacent vertebrae.

In particular, a dynamic stabilizing device, i.e., capable of allowing relative movement between the vertebrae, is disclosed in EP 0 669 109. This vertebral stabilizer comprises a spacing body, which is resistant to compression and is adapted to transfer forces between two screws implanted in the respective vertebrae, and a tensioning cord, which is connected between the two screws described above and passes in an internal longitudinal cavity obtained in the spacing body.

However, this stabilizer has a drawback, due to the fact that it is directly assembled locally on the spinal column after inserting the screws in the vertebrae, with open surgery in a space that is close to the vertebra. Therefore, the surgical procedure that allows to use such stabilization structure is highly invasive, since it is necessary to create close to the vertebra enough space to perform the various steps of assembly, with considerable difficulty for the surgeon, who must arrange and assemble each individual element directly on the vertebra.

Moreover, the stabilizer described above does not allow a transverse connection between screws mounted on different vertebrae in order to transmit forces in a diagonal direction with respect to the axis of the spinal column.

Further, the tensioning cord must be threaded in the spacing body, and this require a higher skill effort for the surgeon.

Moreover, the surgeon may need a stabilizer that has both static and dynamic portions, i.e., he may have to create a hybrid stabilizer, in which the portions can be chosen by the surgeon according to the characteristics of the pathology.

Known types of stabilizer do not allow to create a stabilizer of the hybrid type.

WO2007/060534 A2 in the name of this same Applicant as the present invention, discloses a vertebral stabilizer of the dynamic modular type, which is adapted to be assembled separately from the spinal column and then fitted onto the spinal column in a few seconds.

However, the known type of stabilizer device is unable to adapt to angle variations with which the pedicle screws might be fitted within the vertebrae, and therefore, if the positioning of such pedicle screws is not performed, in two adjacent vertebrae, with the same angle, the surgeon encounters difficulties in fitting the stabilizer device fitted over the head of the pedicle screws.

DISCLOSURE OF THE INVENTION

The aim of the present invention is to provide a device for stabilizing the spinal column which allows connection between adjacent vertebrae, allowing different angles between pedicle screws inserted in adjacent vertebrae.

Within this aim, an object of the present invention is to provide a stabilizer device that can be assembled separately from the spinal column and then fitted onto the spinal column with reduced invasiveness for the patient.

Another object of the present invention is to provide a spinal column stabilizer device that is modular, allowing therefore to provide a hybrid stabilizer device, i.e., a device that is static at one end and dynamic at the opposite end.

Another object of the present invention is to provide a stabilizer device that is highly reliable, relatively simple to provide and at competitive costs.

This aim and these and other objects that will become better apparent hereinafter are achieved by a stabilizer device for the spinal column, comprising a first body and a second body adapted to be mutually connected by a rod-like element, said first and second bodies being adapted to be fitted around first and second pedicle screws, which are adapted to be inserted in turn in two mutually adjacent vertebrae, said first and second bodies being fixable on said pedicle screws, characterized in that said first and second bodies are fork-shaped and adapted to accommodate locking means, said locking means being adapted to pass from a position for accommodating said pedicle screw to a position for locking said pedicle screw within said fork-shaped body.

BRIEF DESCRIPTION OF THE DRAWINGS

Further characteristics and advantages of the invention will become better apparent from the following detailed description of some preferred but not exclusive embodiments of the device according to the present invention, illustrated by way of non-limiting example in the accompanying drawings, wherein:

FIG. 2 is a top plan view of the stabilizer device according to the present invention, in a first embodiment, in an unassembled configuration around a pedicle screw;

FIG. 3 is a top plan view of the stabilizer device according to the present invention, in the first embodiment, in an assembled configuration around the pedicle screw;

FIG. 4 is a top plan view of the stabilizer device according to the present invention, in a second embodiment, in an unassembled configuration around the pedicle screw;

FIG. 5 is a top plan view of the stabilizer device according to the present invention, in the second embodiment, in an assembled configuration around the pedicle screw.

Figure 1:
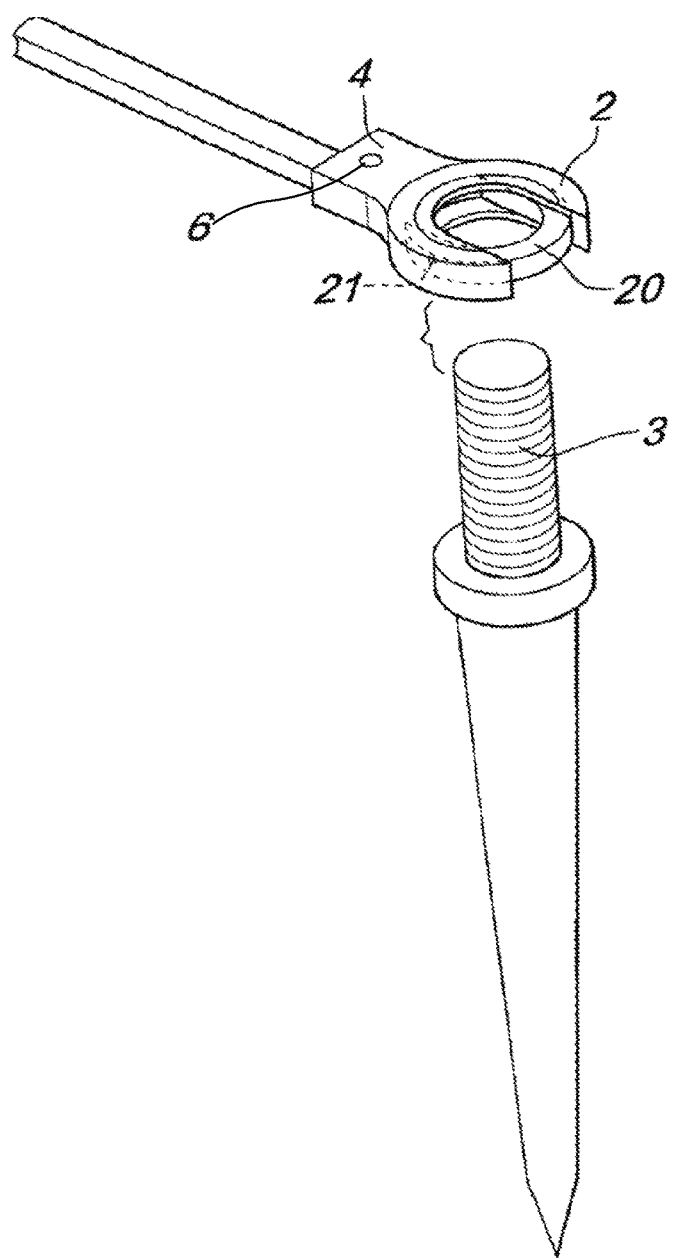
FIG. 1 is an exploded perspective view of a stabilizer device according to the present invention.

With reference to the figures, a stabilizer device according to the present invention, generally designated by the reference numeral 1, comprises a fork-shaped body 2, which is adapted to engage a pedicle screw 3 designed to be inserted in a vertebra.

The fork-shaped body 2 is provided with a portion 4 which blends with the circular portion that forms the fork, the portion 4 having a seat that is adapted to accommodate a rod-like element 5.

Conveniently, the portion 4 has at least one hole 6 that is adapted to allow the insertion of stabilizing means, which are conveniently constituted for example by a cord 7 which is connected to a second fork-shaped body 2 arranged at the opposite end of the rod-like element 5.

Substantially, the stabilizer device according to the invention has first and second fork-shaped bodies 2, which are adapted to be connected by the rod-like element 5 and to engage respectively two pedicle screws 3 arranged respectively in two adjacent vertebrae which are adapted to be mutually stabilized.

The pedicle screws are conveniently headless and cannulated, so that they can be screwed into the vertebrae.

Conveniently, the rod-like element 5 is provided with a pair of mutually opposite lateral recesses 8, which are adapted to accommodate the cord 7 which must be fastened around the rod-like element 5.

Conveniently, the two ends of the cord 7 are provided with respective engagement means 9, which are adapted to allow tensioning of the cord 7.

Conveniently, the engagement means 9 can be provided for example with one end of the cord provided with a set of teeth and the opposite end provided with a receptacle, like a hose clamp.

In this manner, the surgeon can perform, separately from the spinal column, a fastening of the cord 7 around the rod-like element 5 and then, once the stabilizer device has been assembled, said device can be fitted around the pedicle screws 3 that are already accommodated in the holes provided in the vertebrae to be coupled in a stabilized manner.

Conveniently, the rod-like element 5 can be of the rigid type, in which case the presence of the cord 7 is not necessary, or of the elastic type, with which the cord 7 is therefore associated.

In a second embodiment of the device according to the invention, shown in FIGS. 4 and 5, the fork-shaped body 2 is provided in such a manner as to mate with a corresponding fork-shaped body 2 that is arranged in a diametrically opposite position with respect to the pedicle screw 3. In this case, the mating of the two fork-shaped bodies provides a complete disk-like element, which surrounds the pedicle screw 3 completely.

Therefore, differently from the first embodiment, in which the fork-shaped body 2 has a substantially U-shaped internal contour, the body 2 of the second embodiment has a semi-circular internal contour, which is adapted to surround half of the pedicle screw 3, the other half of the screw being surrounded by the corresponding fork-shaped body 2 arranged diametrically opposite the first body.

In this manner it is possible to mutually connect more than two adjacent vertebrae and it is also possible to provide a hybrid modular stabilizer device, i.e., a device that is partially static and partially dynamic, depending on whether the rod-like element 5 is of the rigid or elastic type.

It is in fact possible to connect to each other first and second adjacent vertebrae by using a rigid rod-like element and connect the second vertebra and a third vertebra, which is adjacent to the second vertebra, by using an elastic rod-like element. In this manner a hybrid stabilizer device is obtained.

Conveniently, the mating of two fork-shaped bodies 2 arranged mutually opposite with respect to the pedicle screw 3, as shown in FIGS. 4 and 5, occurs by way of the presence of mating means 15 and 16 provided at each end of the fork.

Substantially, the mating means 15 are constituted for example by a protruding pin provided with a tooth 18, while the mating means 16 have a seat that is adapted to accommodate the pin 15 and the corresponding tooth 18.

Each fork-shaped body therefore has a mating means 15 and a mating means 16 which are adapted to mate complementarily with similar means on the opposite fork-shaped body 2.

Other mating means are of course possible, so long as they are capable of ensuring a stable mating of the two fork-shaped bodies which are mutually opposite with respect to the pedicle screw 3.

The stabilizer device according to the invention, assembled away from the spinal column, is then inserted under the skin of the patient so that the distal fork-shaped body 2 engages the distal pedicle screw 3 and then the proximal fork-shaped body 2 fits on the pedicle screw 3.

In the first embodiment, locking of the fork-shaped body 2 is provided by way of locking means, such as for example an open annular element 20, which is C-shaped and inserted within the U-shaped portion of the fork-shaped body 2.

Such annular element is adapted to rotate freely within said U-shaped portion, so that it can be turned around the pedicle screw 3, as shown in FIG. 3, so as to lock the fork-shaped body 2 around the pedicle screw 3.

The rotation of the annular element 20 can be performed thanks to the presence of a pair of holes 21 arranged at the face of the fork-shaped body 2, which allows the insertion of a tool that allows to turn the annular element 20.

In practice it has been found that the stabilizer device according to the present invention fully achieves the intended aim and objects, since it allows to be assembled away from the spinal column, allows to adapt to different implantation angles of the pedicle screws within the vertebrae, and allows to provide hybrid structures with rigid portions and elastic portions.

The stabilizer device thus conceived is susceptible of numerous modifications and variations, all of which are within the scope of the appended claims; all the details may further be replaced with other technically equivalent elements.

In practice, the materials used, as well as the contingent shapes and dimensions, may be any according to requirements and to the state of the art.

The disclosures in Italian Patent Application No. MI2008A002240 from which this application claims priority are incorporated herein by reference.

Where technical features mentioned in any claim are followed by reference signs, those reference signs have been included for the sole purpose of increasing the intelligibility of the claims and accordingly, such reference signs do not have any limiting effect on the interpretation of each element identified by way of example by such reference signs.

The invention claimed is:

1. A stabilizer device for a spinal column, comprising:
a first body including a first end adapted to be connected to a rod-like element,
said first body including a semi-circular fork-shaped portion, opposite the first end, being adapted to be fitted around a cylindrical portion of a first headless pedicle screw, which is adapted to be inserted into a vertebrae,
said first body being fixable via said semi-circular fork-shaped portion on said cylindrical portions of said headless pedicle screws, and
wherein the first body comprises an upper surface forming a superior semi-circular fork-shaped surface, a lower surface forming an inferior semi-circular fork-shaped surface opposite the upper surface, and a semi-circular recess formed between the upper surface and the lower surface and extending in a direction substantially parallel with the upper surface of the first and that cooperatively engages a locking element, said locking element rotatably coupled in the semi-circular recess between a first position wherein the locking element is completely retained between the upper and lower surfaces and within the semi-circular recess so as to accommodate said headless pedicle screw into said semi-circular fork-shaped portion, and a second position wherein the locking element completes a circular engagement around said cylindrical portion of said headless pedicle screw, thereby locking said pedicle screw within said semi-circular fork-shaped portion.

2. The stabilizer device according to claim 1, wherein said locking element comprises a substantially C-shaped annular element, which is adapted to rotate freely within said first semi-circular fork-shaped portion and to pass from the first position for accommodating said pedicle screw to the second position for locking said pedicle screw when said C-shaped element is rotated about said pedicle screw.

3. The stabilizer device according to claim 1, wherein said first end of said first body has a protruding portion that blends with said body to accommodate said rod-like element.

4. The stabilizer device according to claim 1, wherein said rod-like element is rigid.

5. The stabilizer device according to claim 1, wherein said rod-like element is elastic.

6. The stabilizer device according to claim 1, wherein said locking element is completely contained within said recess when the element is in the first position.

7. The stabilizer device according to claim 1, wherein said first body includes a substantially U-shaped contour, and the recess defines an annular contour formed within the substantially U-shaped contour.

8. A fixing element for fixing a pedicle screw, comprising:

a body, said body comprising first and second fork arms adapted to be fitted at least partially around a cylindrical portion said pedicle screw, said cylindrical portion adapted to extend externally from a pedicle with said pedicle screw inserted in a vertebra body, said first and second fork arms including an upper surface and a lower surface opposite the upper surface, wherein the upper surface forms a continuous superior surface spanning from the first fork arm to the second fork arm and the lower surface forms a continuous inferior surface spanning from the first fork arm to the second fork arm; and a crescent shaped lock element, said crescent shaped lock element movably coupled to said first fork arm within a fork-shaped recess in the body and rotatable from said first fork arm towards said second fork arm such that said crescent shaped lock element extends completely below said upper surface and completely above said lower surface; wherein said recess extends in a direction substantially parallel with the upper surface of the first and second fork arms; wherein said crescent shaped lock element have a first position for accommodating receiving said cylindrical portion of said pedicle screw via an opening formed by said first and second fork arms and a second position for locking said cylindrical portion of said pedicle screw within said body, wherein said crescent shaped lock element is completely housed within said recess when the crescent shaped lock element is in the first position.

9. The fixing element according to claim 8, wherein said lock element is a C-shaped open annular element, which is adapted to be rotated within the fork-shaped recess in said first and second fork arms.

10. The fixing element according to claim 8, wherein the first fork arm and the second fork arm face in opposing directions forming said opening for receiving said cylindrical portion of said pedicle screw on a first end and a u-shape structure on a second end.

11. The fixing element according to claim 8, wherein the first and second fork arms define a substantially U-shaped contour, and the recess defines an annular contour formed within the substantially U-shaped contour.

* * * * *

UNITED STATES PATENT AND TRADEMARK OFFICE
CERTIFICATE OF CORRECTION

PATENT NO. : 9,827,016 B2  
APPLICATION NO. : 14/828714  
DATED : November 28, 2017  
INVENTOR(S) : Calvosa et al.

Page 1 of 1

It is certified that error appears in the above-identified patent and that said Letters Patent is hereby corrected as shown below:

On the Title Page

In Column 1, under "Related U.S. Application Data", Line 3, after "abandoned.", insert:
--¶(30) Foreign Application Priority Data
Dec. 17, 2008 (IT) MI2008A002240--

Signed and Sealed this
Ninth Day of July, 2019

Andrei Iancu
*Director of the United States Patent and Trademark Office*